United States Patent [19]

Kornreich et al.

[11] Patent Number: 5,245,009

[45] Date of Patent: * Sep. 14, 1993

[54] CRF ANTAGONISTS

[75] Inventors: Wayne D. Kornreich, San Diego, Calif.; Jean-Francois Hernandez, Qullins, France; Jean E. F. Rivier, La Jolla, Calif.; Catherine L. Rivier, La Jolla, Calif.; Wylie W. Vale, Jr., La Jolla, Calif.

[73] Assignee: The Salk Institute for Biological Studies, San Diego, Calif.

[*] Notice: The portion of the term of this patent subsequent to Apr. 28, 2007 has been disclaimed.

[21] Appl. No.: 715,752

[22] Filed: Jun. 14, 1991

Related U.S. Application Data

[63] Continuation-in-part of Ser. No. 709,091, May 31, 1991, and a continuation-in-part of Ser. No. 498,814, Mar. 23, 1990, Pat. No. 5,109,111.

[51] Int. Cl.$^5$ .................. C07K 7/38; C07K 7/60; C07K 7/10

[52] U.S. Cl. .................. 530/306; 530/317; 530/321; 530/324; 530/325; 930/21; 930/70; 930/260

[58] Field of Search ............ 530/306, 324, 325, 321, 530/317; 514/9, 2, 805; 930/21, 70, 260

[56] References Cited

U.S. PATENT DOCUMENTS

| | | | |
|---|---|---|---|
| 3,761,459 | 9/1973 | Pless | 530/324 |
| 3,770,715 | 11/1973 | Tesser et al. | 530/324 |
| 4,415,558 | 11/1983 | Vale et al. | 424/177 |
| 4,489,163 | 12/1984 | Rivier et al. | 436/86 |
| 4,594,329 | 6/1986 | Vale et al. | 514/12 |
| 4,605,642 | 8/1986 | Rivier et al. | 514/12 |

FOREIGN PATENT DOCUMENTS 9003392 4/1990 PCT Int'l Appl. .

OTHER PUBLICATIONS

Rivier et al., Proc. Natl. Acad. Sci. USA, vol. 80, pp. 4851-4855, (Aug. 1983).
Rivier et al., Science, vol. 224, pp. 889-891, (May. 22, 1984).
Shibabara et al., The EMBO Journal, vol. 2(5), pp. 775-779, (1983).
Rittel, Proceedings of the Biochemical Society, 56p, vol. 125, (1971).
Hulligen et al., Acta Endocrinologica, vol. 75, pp. 24-32, (1974).

Primary Examiner—Merrell C. Cashion, Jr.
Assistant Examiner—T. D. Wessendorf
Attorney, Agent, or Firm—Fitch, Even, Tabin & Flannery

[57] ABSTRACT

Disclosed are improved CRF peptide antagonists such as those having the formula: Y-D-Phe-$R_{13}$-Leu-Leu-Arg-$R_{17}$-$R_{18}$-Leu-$R_{20}$-Nle-$R_{22}$-$R_{23}$-$R_{24}$-$R_{25}$-$R_{26}$-Leu-$R_{28}$-$R_{29}$-Gln-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein Y is Ac or hydrogen; $R_{13}$ is His, Tyr or Glu; $R_{17}$ is Cys, Glu, Asn or Lys; $R_{18}$ is Val, Nle or Met; $R_{20}$ is D-Cys, Glu, D-Glu, Aib or D-Ala; $R_{22}$ is Ala, Aib, Thr, Asp or Glu; $R_{23}$ is Arg, Orn, Har or Lys; $R_{24}$ is Ala or Aib; $R_{25}$ is Asp or Glu; $R_{26}$ is Gln, Asn or Lys; $R_{28}$ is Ala or Aib; $R_{29}$ is Gln, Aib or Glu, $R_{31}$ is Ala or Aib; $R_{32}$ is His, Aib, Gly, Tyr or Ala; $R_{33}$ is Ser, Aib, Asn, Leu, Thr or Ala; $R_{34}$ is Asn or Aib; $R_{36}$ is Lys, Orn, Arg, Har or Leu; $R_{37}$ is Leu or Try; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln. Specific CRF antagonists disclosed include [D-Phe[12], D-Ala[20], Nle[21,38],]-rCRF(12-41), [D-Phe[12], Nle[21,38], Aib[33]]-rCRF(12-41) and (c 17-20) [D-Phe[12], Cys[17], D-Cys[20], Nle[21,38]]-rCRF(12-41).

3 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

```
Ser  Gln  Glu  Pro  Pro  Ile  Ser  Leu  Asp  Leu  Thr  Phe  His  Leu  Leu  Arg
1                 5                        10                            15

Glu  Val  Leu  Glu  Met  Thr  Lys  Ala  Asp  Gln  Leu  Ala  Gln  Gln  Ala  His
               20                      25                      30

Ser  Asn  Arg  Lys  Leu  Leu  Asp  Ile  Ala
          35                 40
```

( 2 ) INFORMATION FOR SEQ ID NO:2:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

```
Ser  Glu  Glu  Pro  Pro  Ile  Ser  Leu  Asp  Leu  Thr  Phe  His  Leu  Leu  Arg
1                 5                        10                            15

Glu  Val  Leu  Glu  Met  Ala  Arg  Ala  Glu  Gln  Leu  Ala  Gln  Gln  Ala  His
               20                      25                      30

Ser  Asn  Arg  Lys  Leu  Met  Glu  Ile  Ile
          35                 40
```

( 2 ) INFORMATION FOR SEQ ID NO:3:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

```
Ser  Gln  Glu  Pro  Pro  Ile  Ser  Leu  Asp  Leu  Thr  Phe  His  Leu  Leu  Arg
1                 5                        10                            15

Glu  Met  Leu  Glu  Met  Ala  Lys  Ala  Glu  Gln  Glu  Ala  Glu  Gln  Ala  Ala
               20                      25                      30

Leu  Asn  Arg  Leu  Leu  Leu  Glu  Glu  Ala
          35                 40
```

(2) INFORMATION FOR SEQ ID NO:4:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:4:

Ser Glu Glu Pro Pro Ile Ser Leu Asp Leu Thr Phe His Leu Leu Arg
1               5                   10                  15
Glu Val Leu Glu Met Ala Arg Ala Glu Gln Leu Ala Gln Gln Ala His
          20                  25                  30
Ser Xaa Arg Lys Leu Met Glu Ile Ile
      35                  40

CRF ANTAGONISTS

This invention was made with Government support under grant numbers HD-13527 and DK-26741 awarded by the National Institutes of Health. The Government has certain rights in this invention.

This application is a continuation-in-part of U.S. Ser. No. 07/709,091 filed May 31, 1991, and Ser. No. 07/498,814 filed Mar. 23, 1990, now U.S. Pat. No. 5,109,111.

This invention is directed to peptides and to methods for pharmaceutical treatment of mammals using such peptides. More specifically, the invention relates to analogs of the hentetracontapeptide CRF, particularly antagonists thereof, to pharmaceutical compositions containing such CRF analogs and to methods of treatment of mammals using such CRF analogs.

BACKGROUND OF THE INVENTION

Experimental and clinical observations have supported the concept that the hypothalamus plays a key role in the regulation of adenohypophysial corticotropic cells' secretory functions. Although over 25 years ago it was demonstrated that factors present in the hypothalamus would increase the rate of ACTH secretion by the pituitary gland, when incubated in vitro or maintained in an organ culture, a physiologic corticotropin releasing factor (CRF) was not characterized until ovine CRF (oCRF) was characterized in 1981. As disclosed in U.S. Pat. No. 4,415,558, oCRF was found to have the formula (SEQ ID NO:1): Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala wherein the c-terminus is amidated. oCRF lowers blood pressure in mammals when injected peripherally and stimulates the secretion of ACTH and $\beta$-endorphin.

Rat CRF(rCRF) was later isolated, purified and characterized as a hentetracontapeptide having the formula (SEQ ID NO:2): Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lsy-Leu-Met-Glu-Ile-Ile, wherein the C-terminus is amidated, as described in U.S. Pat. No. 4,489,163. It is sometimes referred to as rat amunine. The formula of human CRF has now been determined to be the same as that of rCRF, and the terms rCRF and hCRF are used interchangeably. A CRF analog has been developed having a high alpha-helical forming potential and the formula (SEQ ID NO:3): Ser-Gln-Glu-Pro-Pro-Ile-Ser-Leu-Asp-Leu-Thr-Phe-His-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala, wherein the C-terminus is amidated; it is referred to as AHC (alpha- helical CRF) and is described in U.S. Pat. No. 4,594,329.

Synthetic rCRF, oCRF and AHC stimulate ACTH and $\beta$-endorphin-like activities ($\beta$-END-LI) in vitro and in vivo and substantially lower blood pressure when injected peripherally. Antagonists of these compounds are disclosed in U.S. Pat. No. 4,605,642, issued Aug. 12, 1986.

SUMMARY OF THE INVENTION

Analogs of these peptides having improved biological activity, e.g. CRF peptides have been discovered which exhibit longer lasting biological activity, and certain analogs which are of particular interest are novel CRF antagonists that have improved biological properties in comparison to known CRF antagonists. These peptides preferably have a specific D-isomer substitution in the 20-position or have Aib in certain positions, i.e. from position 20 to the C-terminus; among the preferred analogs are those which have a cyclizing bond between the residues in the 17- and 20-positions. The peptide antagonists preferably optionally also have D-Phe in the 12-position and norleucine in the 21 and 38 positions. Other optional substitutions may also be made throughout the molecule as previously taught. For example, the Leu residue in the 37-position can be substituted with a methyl group on its $\alpha$-carbon atom, as can be other Leu residues throughout the molecule, and such substitutions, both alone and in combination with the aforementioned substitutions, are considered to enhance biopotency. Beginning at the N-terminus, the peptide is shortened by the deletion of 8 to about 11 residues to produce the antagonists, and is preferably shortened by deletion of 11 residues.

Pharmaceutical compositions in accordance with the invention include such CRF analogs, including the antagonists, or nontoxic addition salts thereof, dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, $\beta$-endorphin, $\beta$-lipotropin, other products of the pro-opiomelanocortin gene and coricosterone and/or for affecting mood, behavioral and gastrointestinal functions and autonomic nervous system activities. CRF agonists may be used for the lowering of blood pressure.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline, Abu=L-2-aminobutyric acid, Dbu=L-2,4-diaminobutyric acid, Dpr=L-2,3-diaminopropionic acid, and Har=L-homoarginine. In addition the following abbreviations are used: CML=$C^\alpha CH_3$-L-leucine; Aib=$C^\alpha CH_3$-L-alanine or 2-aminoisobutyric acid; Nal=L-$\beta$-(1- or 2-naphthyl) alanine and Pal=L-$\beta$-(2-,3- or 4-pyridyl) alanine.

A preferred group of antagonists are those having the formula: Y-D-Phe-$R_{13}$-Leu-Leu-Arg-$R_{17}$-$R_{18}$-Leu-$R_{20}$-Nle-$R_{22}$-$R_{23}$-$R_{24}$-$R_{25}$-$R_{26}$-Leu-$R_{28}$-$R_{29}$-Gln-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein Y is Ac or hydrogen; $R_{13}$ is His, Tyr or Glu; $R_{18}$ is Cys, Glu, Asn or Lys; $R_{18}$ is Val, Nle or Met; $R_{20}$ is D-Cys, Glu, D-Glu, Aib or D-Ala; $R_{22}$ is Ala, Aib, Thr, Asp or Glu; $R_{23}$ is Arg, Orn, Har or Lys; $R_{24}$ is Ala or Aib; $R_{25}$ is Asp or Glu; $R_{26}$ is Gln, Asn or Lys; $R_{28}$ is Ala or Aib; $R_{29}$ is Gln, Aib or Glu, $R_{31}$ is Ala or Aib; $R_{32}$ is His, Aib, Gly, Tyr or Ala; $R_{33}$ is Ser, Aib, Asn, Leu, Thr or Ala; $R_{34}$ is Asn or Aib; $R_{36}$ is Lys, Orn, Arg, Har or Leu;

$R_{37}$ is Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln, with the proviso that $R_{20}$ is either D-Ala or D-Cys or $R_{34}$ is Aib; or a nontoxic addition salt thereof. Analogs of this group which have been found to be particularly biopotent are: [D-Phe$^{12}$, D-Ala$^{20}$, Nle$^{21,38}$]-rCRF(12–41), [D-Phe$^{12}$, Nle$^{21,38}$, Aib$^{33}$]-rCRF(12–41) and (c 17–20) [D-Phe$^{12}$, Cys$^{17}$, D-Cys$^{20}$, Nle$^{21,38}$]-rCRF(12–41).

Another preferred group of antagonists are those having the formula: Y-D-Phe-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-$R_{27}$-R$_{28}$-$R_{29}$-Gln-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein Y is Ac or hydrogen; $R_{13}$ is His, Tyr or Glu; $R_{14}$ is CML or Leu; $R_{15}$ is CML or Leu; $R_{17}$ is CML, Glu, Asn or Lys; $R_{18}$ is Val, Nle or Met; $R_{19}$ is CML or Leu; $R_{20}$ is D-Cys, Glu, D-Glu, Aib or D-Ala; $R_{22}$ is Ala, Aib, Thr, Asp or Glu; $R_{23}$ is Arg, Orn, Har or Lys; $R_{24}$ is Ala or Aib; $R_{25}$ is Asp or Glu; $R_{26}$ is Gln, Asn or Lys; $R_{27}$ is CML or Leu; $R_{28}$ is Ala or Aib; $R_{29}$ is Gln, Aib or Glu, $R_{31}$ is Ala or Aib; $R_{32}$ is His, Aib, Gly, Tyr or Ala; $R_{33}$ is Ser, Aib, Asn, Leu, Thr or Ala; $R_{34}$ is Asn or Aib; $R_{36}$ is Lys, Orn, Arg, Har or Leu; $R_{37}$ is CML, Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln, with the proviso that at least one of $R_{14}$, $R_{15}$, $R_{17}$, $R_{19}$ and $R_{27}$ is CML; or a nontoxic addition salt thereof. Analogs of this group which have been found to be particularly biopotent are: [D-Phe$^{12}$, CML$^{14}$, Nle$^{21,38}$]-rCRF(12–41), [D-Phe12, CML15, Nle$^{21,38}$]-rCRF(12–41), [D-Phe$^{12}$, CML$^{17}$, Nle$^{21,38}$]-rCRF(12–41), [D-Phe$^{12}$, CML$^{27}$, Nle$^{21,38}$]-rCRF(12–41), and [D-Phe$^{12}$, CML$^{17,37}$, Nle$^{21,38}$]-rCRF(12–41).

Still another group of preferred antagonists are those having the formula:

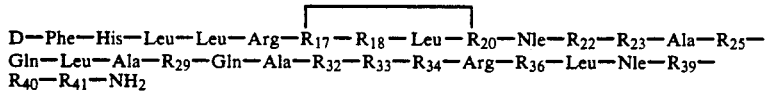

D—Phe—His—Leu—Leu—Arg—$R_{17}$—$R_{18}$—Leu—$R_{20}$—Nle—$R_{22}$—$R_{23}$—Ala—$R_{25}$—Gln—Leu—Ala—$R_{29}$—Gln—Ala—$R_{32}$—$R_{33}$—$R_{34}$—Arg—$R_{36}$—Leu—Nle—$R_{39}$—$R_{40}$—$R_{41}$—NH$_2$ wherein $R_{17}$ is Cys, Abu, Glu, Asp, Dpr, Dbu, Orn or Lys; $R_{18}$ is Val, Nle or Met; $R_{20}$ is D-Cys, D-Glu, D-Asp, D-Dpr, D-Dbu, D-Orn or D-Lys; $R_{22}$ is Ala or Thr; $R_{23}$ is Arg or Lys; $R_{25}$ is Asp or Glu; $R_{29}$ is Gln or Glu; $R_{32}$ is His or Ala; $R_{33}$ is Ser or Leu; $R_{34}$ is Asn or Aib; $R_{36}$ is Lys or Leu; $R_{39}$ is Glu or Asp; $R_{40}$ is Ile or Glu; and $R_{41}$ is Ile or Ala; or a nontoxic addition salt thereof.

In a broader sense, the invention provides antagonists of CRF having the following formula: Y-$R_9$-$R_{10}$-$R_{11}$-$R_{12}$-$R_{13}$-Leu-Leu-Arg-$R_{17}$-$R_{18}$-$R_{19}$-$R_{20}$-$R_{21}$-$R_{22}$-$R_{23}$-R$_{24}$-$R_{25}$-$R_{26}$-$R_{27}$-$R_{28}$-$R_{29}$-Gln-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein Y is an acyl group having 7 or less carbon atoms or hydrogen; $R_9$ is desR$_9$ or Asp; $R_{10}$ is desR$_{10}$ or Leu; $R_{11}$ is desR$_{11}$, Thr or Ser; $R_{12}$ is (Q)D-Phe, D-Tyr, D-Leu, D-His, D-Nal, D-Pal, D-Ile, D-Nle, D-Val, D-Met, Phe or Leu; Q is H, 4Cl or 4F; $R_{13}$ is His, Tyr or Glu; $R_{17}$ is Cys, CML, Glu, Asn or Lys; $R_{18}$ is Val, Nle or Met; $R_{19}$ and $R_{24}$ are selected from the group consisting of Leu, Ile, Ala, Aib, Gly, Val, Nle, Phe, Asn and Gln; $R_{20}$ is D-Cys, Aib, D-Glu, Glu or D-Ala; $R_{21}$ is Nle, Met, Nva, Ile, Ala, Leu, Val, Phe, Asn or Gln; $R_{22}$ is Ala, Aib, Thr, Asp or Glu; $R_{23}$ is Arg, Orn, Har or Lys; $R_{25}$ is Asp or Glu; $R_{26}$ is Gln, Asn or Lys; $R_{27}$ is Leu, Ile, Ala, Val, Nva, Met, Nle, Phe, Asp, Asn, Gln or Glu; $R_{28}$ is Ala, Aib, Arg or Lys; $R_{29}$ is Gln, Aib or Glu; $R_{31}$ is Ala or Aib; $R_{32}$ is His, Aib, Gly, Tyr or Ala; $R_{33}$ is Ser, Aib, Asn, Leu, Thr or Ala; $R_{34}$ is Aib or Asn; $R_{36}$ is Lys, Orn, Arg, Har or Leu; $R_{37}$ is Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; wherein CML may be substituted for Leu; or a nontoxic addition salt thereof, provided, however, that $R_{20}$ is D-Cys, Aib or D-Ala, or one of $R_{22}$, $R_{24}$, $R_{28}$, $R_{29}$, $R_{31}$, $R_{32}$, $R_{33}$, $R_{34}$, $R_{39}$ or $R_{40}$ is Aib. Antagonists in accordance with this formula exhibit excellent binding to pituitary receptors for native CRF.

In a still broader sense, there are provided analogs of CRF of the following formula: Y-$R_1$-$R_2$-$R_3$-$R_4$-R$_5$-Ile-Ser-$R_8$-$R_9$-Leu-$R_{11}$-$R_{12}$-$R_{13}$-$R_{14}$-Leu-Arg-R$_{17}$-$R_{18}$-$R_{19}$-$R_{20}$-$R_{21}$-$R_{22}$-$R_{23}$-$R_{24}$-$R_{25}$-$R_{26}$-R$_{27}$-$R_{28}$-$R_{29}$-Gln-Ala-$R_{32}$-$R_{33}$-$R_{34}$-Arg-$R_{36}$-$R_{37}$-$R_{38}$-$R_{39}$-$R_{40}$-$R_{41}$-NH$_2$ wherein Y is an acyl group having 7 or fewer carbon atoms or hydrogen; $R_1$ is Ser, D-Ser or desR$_1$; $R_2$ is Glu, Gln, pGlu, D-pGLU or desR$_2$; $R_3$ is Glu, Gly, D-Tyr or desR$_3$; $R_4$ is Pro, D-Pro or desR$_4$; $R_5$ is Pro or desR$_5$; $R_8$ and $R_{19}$ are selected from the group consisting of Leu, Ile, Ala, Gly, Val, Nle, Phe and Glyn; $R_9$ is Asp or Glu; $R_{11}$ is Thr or Ser; $R_{12}$ is Phe, D-Phe, Leu, Ala, Ile, Gly, Val, Nle or Gln; $R_{13}$ is His, Tyr or Glu; $R_{14}$ is Leu or Met; $R_{17}$ is Glu, CML, Cys or Lys; $R_{18}$ is Val, Nle or Met; $R_{20}$ is Ala, D-Ala, D-Cys, Aib, D-Glu or Glu; $R_{21}$ is Arg, Met, Nva, Ile, Ala, Leu, Nle, Val, Phe or Gln; $R_{22}$ is Ala, Thr, Asp or Glu; $R_{23}$ is Arg, Orn, Har or Lys; $R_{24}$ is Ala, D-Ala, Met, Leu, Ile, Gly, Val, Nle, Phe and Gln; $R_{25}$ is Glu, Ala or Asp; $R_{26}$ is Gly, Gln, Asn or Lys; $R_{27}$ is Leu, Ile, Ala, Val, Nva, Met, Nle, Phe, Asp, Asn, Gln or Glu; $R_{28}$ is Ala, Arg or Lys; $R_{29}$ is Gln, Ala or Glu; $R_{32}$ is Leu, His, D-His, Gly, Tyr or Ala; $R_{33}$ is Ile, Ser, Asn, Leu, Thr or Ala; $R_{34}$ is Aib or Asn; $R_{36}$ is Asn, Lys, Orn, Arg, Har or Leu; $R_{37}$ is Leu or Tyr; $R_{38}$ is Met, Nle or Leu; $R_{39}$ is Ala, Glu or Asp; $R_{40}$ is Ile, Thr, Glu, Ala, Val, Leu, Nle, Phe, Nva, Gly, Asn or Gln; $R_{41}$ is Ile, Ala, Gly, Val, Leu, Nle, Phe or Gln; wherein CML can be substituted for Leu; provided however that $R_{20}$ is D-Ala or $R_{34}$ is Aib, as well as nontoxic salts thereof.

The peptides are synthesized by a suitable method, such as by exclusively solid-phase techniques, by partial solid-phase techniques, by fragment condensation or by classical solution addition.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following formula: $X^1$-D-Phe-$R_{13}(X^7$ or $X^5)$-Leu-Leu-Arg$(X^3)$-$R_{17}(X^4,X^5$ or $X^6)$-$R_{18}$-Leu-$R_{20}(X^5$ or $X^8)$-Nle-$R_{22}(X^2$ or $X^5)$-$R_{23}(X^3$ or $X^6)$-$R_{24}$-$R_{25}(X^5)$-$R_{26}(X^4$ or $X^6)$-Leu-$R_{28}$-$R_{29}(X^4$ or $X^5)$-Gln$(X^4)$-$R_{31}$-$R_{32}(X^7)$-$R_{33}(X^2$ or $X^4)$-$R_{34}(X^4)$-Arg$(X^3)$-$R_{36}(X^3$ or $X^6)$-$R_{37}(X^7)$-Nle-$R_{39}(X^5)$-$R_{40}(X^2, X^4$ or $X^5)$-$R_{41}(X^4)$-$X^9$ wherein: the R-groups are as hereinbefore defined.

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl, acrylyl(acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl metholoxycarbonyl (FMOC), cyclopentyloxy-carbonyl, adamantyloxycarbonyl, and cyclohexyloxy-carbonyl; and (5) thiourethan-type protecting groups, such as phenylthiocarbonyl. The preferred alpha-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the quanidino group of Arg or Har preferably selected from the class consisting of nitro, p-toluenesulfonyl(Tos), Z, adamantyloxycarbonyl and BOC, or is hydrogen. Tos is most preferred.

$X^4$ is hydrogen or a protecting group, preferably xanthyl(Xan), for the amido group of Asn or Gln. Asn or Gln is preferably coupled without side chain protection in the presence of hydroxybenzotriazole (HOBt).

$X^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (Ot-Bu). OChx is preferred for a BOC strategy.

$X^6$ is hydrogen or a protecting group for the side chain amino substituent of Lys or Orn. Illustrative or suitable side chain amino-protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore. 2-Cl-Z is preferred for a BOC strategy.

When His is present, $X^7$ is hydrogen or a protecting group for the imidazole nitrogen such as Tos or 2,4-dinitrophenyl(DNP), and when Tyr is present, $X^7$ is hydrogen or a protecting group for the hydroxy group such as DCB. When Met is present, the sulfur may be protected, if desired, with oxygen.

$X^8$ is a protecting group for the sulfhydryl group of Cys, preferably p-methoxybenzyl(MeOBzl), p-methylbenzyl, acetamidomethyl, trityl or Bzl; or a suitable protecting group for an amino side chain which is removable without simultaneously removing the protecting group $X^6$, e.g. a base-labile group such as Fmox; or a suitable labile protecting group for a carboxyl side chain which is removable without simultaneously removing the protecting group $X^5$, e.g., a base-labile group such as OFm (fluorenylmethyl ester); or is a direct bond between the residues in the 17- and 20-positions when the cyclic form results from a carba or dicarba bond.

The selection of a side chain amino protecting group is not critical except that it must be one which is not removed during deprotection of the alpha-amino groups during the synthesis. Hence, the alph-amino protecting group and the side chain amino protecting group cannot be the same.

$X^9$ is $NH_2$, a protecting group such as an ester or an anchoring bond used in solid phase synthesis for linking to a solid resin support, preferably one represented by the formula: —NH-benzhydrylamine (BHA) resin support and —NH-paramethylbenzhydrylamine (MBHA) resin support. Cleavage from a BHA or MBHA resin directly gives the CRF analog amide. By employing a methyl-derivative of such a resin, a methyl-substituted amide can be created, which is considered to be the equivalent thereof.

In the formula for the intermediate, at least one of $X^1$, $X^2$, $X^3$, $X^4$, $X^5$, $X^6$, $X^7$ and $X^8$ is a protecting group or $X^9$ includes resin support. The particular amino acid chosen for each R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

If an acyl group is present at the N-terminus, as represented by Y, acetyl, formyl, acrylyl and benzoyl are preferred.

Thus, in one aspect, there is also provided a process for the manufacture of compounds comprising (a) forming a peptide intermediate, as defined hereinbefore, having at least one protective group wherein: $X^1$, $X^2$, $X^3$, $X^4$, $X^5$, $X^6$, $X^7$ and $X^8$ are each either hydrogen or a protective group, and $X^9$ is either a protective group or an anchoring bond to resin support or $NH_2$ and (b) splitting off the protective group or groups or the anchoring bond from said peptide intermediate and (c) if desired, converting a resulting peptide into a nontoxic addition salt thereof.

When the peptides are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for an antagonist based upon human CRF can be prepared by attaching alpha-amino-protected Ile to a BHA resin.

Ile protected by BOC is coupled to the BHA resin using methylene chloride and dimethylformamide (DMF). Following the coupling of BOC-Ile to the resin support, the alpha-amino protecting group is removed, as by using trifluoracetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature, Other standard cleaving reagents and conditions for removal of specific alpha-amino protecting groups may be used as described in Schroder & Lubke, "The Peptides", 1 pp 72–75 (Academic Press 1965).

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCC) and N,N'-diisopropyl carbodiimide(DICI).

Activating or coupling reagents for use in the solid phase synthesis of the peptides are well known in the peptide art. Examples of suitable activating reagents are carbodiimides, such as N,N'-diisopropyl carbodiimide and N-ethyl-N'-(3-dimethylaminopropyl) carbodiimide. Other activating reagents and their use in peptide coupling are described by Schroder & Lubke, supra, in Chapter III and by Kapoor, J. Phar. Sci., 59, pp 1–27 (1970). P-nitrophenyl ester (ONp) can also be used to activate the carboxyl end of Asn or Gln for coupling. For example, BOC-Asn(ONp) can be coupled overnight using one equivalent of HOBt in a 50% mixture of DMF and methylene chloride.

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., Anal. Biochem. 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., Biopolymers, 1978, 17, pp. 1927–1938.

After the desired amino acid sequence has been completed, the intermediate peptide is removed from the resin support unless it is desired to first form a cyclizing bond while attached to the resin, as described hereinafter. Removal is effected by treatment with a reagent, such as liquid hydrogen fluoride (HF), which not only cleaves the peptide from the resin but also cleaves all remaining side chain protecting groups $X^2$, $X^3$, $X^4$, $X^5$, $X^6$ and $X^7$ and the alpha-amino protecting group $X^1$, if still present (unless it is an acyl group which is intended to be present in the final peptide), to obtain the peptide. When using hydrogen fluoride for cleaving, anisole or cresole and methylethyl sulfide are included in the reaction vessel as scavengers. When Met is present in the sequence, the BOC protecting group may be cleaved with trifluoracetic acid(TFA)/ethanedithiol prior to cleaving the peptide from the resin to eliminate S-alkylation.

When a cyclizing bond between two Cys residues in positions 17 and 20 is used, cyclization of the cleaved linear peptide is preferably effected, as opposed to cyclizing the peptide while a part of the peptidoresin. To effect such a disulfide cyclizing linkage, the fully protected peptide can be cleaved from a benzyhydrylamine resin or the like at 0° C. with hydrofluoric acid (HF).

Using other protocols where an amide cyclizing linkage is used, cyclization may be carried out while the partially protected peptide remains attached to the resin as disclosed in A. M. Felix et al., Peptides, Proceedings of the Tenth American Peptide Symposium, May 1987, 465–467 (1988). Such a procedure effectively creates an amide cyclizing bond between the two desired side chains while other residues, such as Asp, Glu and/or Lys, retain their side-chain protection.

The cyclizing step for the CRF peptide analog depends, of course, upon the type of linkage which is desired between the residues in the 17- and 20-positions. When residues of D- or L-Cys are included in both the 17- and 20-positions, it is often more convenient to carry out the cyclizing step following the cleavage from the resin and the removal of all of the protecting groups from the peptide. The cyclic form of the peptide is obtained by oxidizing using a ferricyanide solution, preferably as described in Rivier et al., Biopolymers, Vol. 17 (1978), 1927–38, or by air oxidation, or in accordance with other known procedures.

When the cyclization is via an amide bond between a side-chain amino group of the 17-position residue and a side-chain carboxyl group of the 20-position residue, or vice-versa, it is preferably to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 4,661,472, issued Apr. 28, 1987. Preferably cyclization is accomplished by using a base-labile protecting group. e.g., OFm, for the carboxyl side-chain of the residue to be involved in the amide-bond bridge and using Fmoc as a protecting group for the amino side chain on the other residue that is to be involved. The α-amino protecting group on the 1-position residue, whether or not it is to be acylated, and all of the other side-chain protecting groups remain in place while the two base-labile groups are removed using piperidine or the like. Following this selective removal, the reaction to accomplish cyclization is carried out by treating with BOP which effects substantially complete generation of the amide bond. Following cyclization, the peptide is completely deprotected and cleaved from the resin using a reagent, such as HF. Optionally a BOC-protecting group can be first removed using TFA.

Alternatively, cyclizations of peptides by such amide linkages can also be effected using teachings of U.S. Pat. Nos. 4,115,554, (Sep. 19, 1978); 4,144,805 (Jan. 9, 1979); 4,140,767 (Feb. 20, 1979); 4,161,521 (Jul. 17, 1979);

4,191,754 (Mar. 4, 1980); 4,238,481 (Dec. 9, 1980); 4,244,947 (Jan. 13, 1981); and 4,261,885 (Apr. 14, 1981).

Analogs of CRF including the equivalent of modified cysteine residues in the 17- and 20-positions wherein the disulfide linkage has been replaced by —CH$_2$- linkage are referred to as dicarba; if only one of the sulfhydryl groups is replaced by a CH$_2$-group, it is referred to as carba. Viewed from the aspect of the ultimate peptide, the location which would otherwise have been occupied by a Cys residue instead contains a residue of alpha-amino butyric acid (Abu). When preparing peptides having such a dicarba or carba-S linkage, the procedure set forth in U.S. Pat. No. 4,161,521 is preferably employed (the disclosure of which is incorporated herein by reference) so that, in the peptide intermediate, $X^8$ is a direct bond to the other residue.

The following Example sets forth a preferred method for synthesizing CRF antagonists by the solid-phase technique.

EXAMPLE I

The synthesis of the (cyclo 17–20) [D-Phe$^{12}$, Cys$^{17}$, D-Cys$^{20}$, Nle$^{21,38}$]-human CRF (12–41) having the formula:

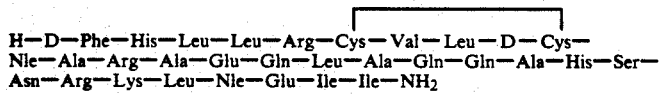

H—D—Phe—His—Leu—Leu—Arg—Cys—Val—Leu—D—Cys—
Nle—Ala—Arg—Ala—Glu—Gln—Leu—Ala—Gln—Gln—Ala—His—Ser—
Asn—Arg—Lys—Leu—Nle—Glu—Ile—Ile—NH$_2$ is conducted in a stepwise manner on a MBHA hydrochloride resin, such as available from Bachem, Inc., having a substitution range of about 0.1 to 0.7 mmoles/gm. resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | CH$_2$Cl$_2$ wash - 80 ml. (2 times) | 3 |
| 2 | Methanol(MeOH) wash - 30 ml. (2 times) | 3 |
| 3 | CH$_2$Cl$_2$ wash - 80 ml. (3 times) | 3 |
| 4 | 50 percent TFA plus 5 percent 1,2-ethanedithiol in CH$_2$Cl$_2$ - 70 ml. (2 times) | 12 |
| 5 | Isopropanol wash - 80 ml. (2 times) | 3 |
| 6 | TEA 12.5 percent in CH$_2$Cl$_2$ - 70 ml. (2 times) | 5 |
| 7 | MeOH wash - 40 ml. (2 times) | 2 |
| 8 | CH$_2$Cl$_2$ wash - 80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30–300 |

Coupling of BOC-Ile results in the substitution of about 0.35 mmol. Ile per gram of resin. All solvents that are used are carefully degassed, preferably by sparging with an inert gas, e.g. helium or nitrogen.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser. BOC-Asn or BOC-Gln is coupled in the presence of one equivalent of DCC and two equivalents of HOBt in a 50% mixture of DMF and methylene chloride. 2-Cl-Z is used as the protecting group for the Lys side chain. Tos is used to protect the quanidino group of Arg and the imidazole group of His, and the side chain carboxyl group of Glu is protected by OChx. At the end of the synthesis, the following composition is obtained: BOC-D-Phe-His(Tos)-Leu-Leu-Arg(Tos)-Cys(MeOBzl)-Val-Leu-D-Cys(MeOBzl)-Nle-Ala-Arg(Tos)-Ala-Glu(OChx)-Gln-Leu-Ala-Gln-Gln-Ala-His(Tos)-Ser(Bzl)-Asn-Arg(Tos)-Lys(2-Cl-Z)-Leu-Nle-Glu(OChx)-Ile-Ile-MBHA resin support.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0° C. for one and one-half hours. After elimination of the HF under high vacuum, the resin-peptide is washed with dry diethyl ether, and the peptides are then extracted with de-gassed 2N aqueous acetic acid and separated from the resin by filtration.

The peptide is then air-oxidized for about 48 hours at about 4° C. and then for about 3 more days at room temperature (or until complete disappearance of —SH as measured by the Ellman test—see *Archives Biochem. Biophys.* 82, 1959, p. 70) to create a disulfide ilnkage between the cysteine residues in each molecule.

The cleaved, deprotected and cyclic peptide is then dissolved in 0–5% acetic acid and subjected to purification which may include Sephadex G-50 fine gel filtration.

The peptide is purified by gel permeation followed by semi-preparative HPLC as described in Rivier et al., *Peptides: Structure and Biological Function* (1979) pp. 125–128, and Rivier et al. *J. Chromatography* (1983). The chromatographic fractions are carefully monitored by HPLC, and only the fractions showing substantial purity are pooled.

Specific optical rotation of the hCRF peptide, which is synthesized and purified in the foregoing manner, is measured on a Perkin Elmer Model 241 Plarimeter as $[\alpha]_D^{22} = -31° \pm 1.0$ (c=1 in 50% acetic acid) (without correction for the presence of H$_2$O and TFA); it has a purity of greater than about 95%. Purity is further confirmed by mass spectroscopy (MS) and capillary zone electrophoresis.

To check whether the precise sequence is achieved, the CRF analog is hydrolyzed in sealed evacuated tubes containing 4 molar methane sulfonic acid, 3 μl of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 30-residue peptide structure has been obtained.

EXAMPLE II

The peptide [D-Phe$^{12}$, D-Ala$^{20}$, Nle$^{21,38}$]-rCRF (12–41) having the formula: H-D-Phe-His-Leu-Leu-Arg-Glu-Val-Leu-D-Ala-Nle-Ala-Arg-Ala-Glu-Gln-Leu-Ala-Gln-Gln-Ala-His-Ser-Asn-Arg-Lys-Leu-Nle-Glu-Ile-Ile-NH$_2$ is synthesized. The peptide is biopotent and inhibits the secretion of ACTH and β-END-LI in response to various stimuli.

Specific optical rotation of the CRF peptide, which is synthesized and purified in the foregoing manner, is measured on a Perkin Elmer Model 241 Polarimeter as $[\alpha]_D^{22} = -33° \pm 1.0$ (c=1 in 50% acetic acid) (without correction for the presence of $H_2O$ and TFA); it has a purity of greater than about 95%.

Amino acid analysis of the resultant, purified peptide is consistent with the formula for the prepared peptide and confirms that the 30-residue peptide structure is obtained.

EXAMPLE III

The peptide [D-Phe$^{12}$, Nle$^{21,38}$, Aib$^{33}$]-rCRF (12–41) having the formula: H-D-Phe-His-Leu-Leu-Arg-Glu-Val-Leu-Glu-Nle-Ala-Arg-Ala-Glu-Gln-Leu-Ala-Gln-Gln-Ala-His-Ser-Aib-Arg-Lys-Leu-Nle-Glu-Ile-Ile-$NH_2$ is synthesized. The peptide is biopotent and inhibits the secretion of ACTH and β-END-LI in response to various stimuli.

The antagonist peptide prepared in Example I is tested using the procedure set forth in detail in J. Rivier et al., Science, 224, 889–891 (1984) to determine its effect in blocking by 50% the secretion of ACTH stimulated by a 1 nM dose of oCRF. Compared to AHC(9–41), a potent CRF antagonist which was disclosed in U.S. Pat. No. 4,605,642, this peptide was about 7 times as potent, i.e. 6.96(2.9–15.9). The specificity of this inhibition is demonstrated by the finding of no effect of the standard antagonist on GRF-stimulated secretion of GH, GnRH-stimulated secretion of LH and FSH or TRF-stimulated secretion of TSH and prolactin. Similar testing shows that the peptide prepared in Example II is more than 3 times as potent as AHC(9–41), and that the peptide prepared in Example III is about 14 times as potent, i.e. 13.56 (6.7–27.4).

The in vivo effect of CRF antagonists is tested by monitoring the spontaneous ACTH release by adrenalectomized rats. The iv injection of 3 mg/kg BW (about 2.7 nmole) is considered to cause a marked decrease in plasma ACTH levels (measured as described in Vale et al. Science, 213, 1394, 1981), which is statistically significant. In the intact, non-anesthetized rats, the antagonists are considered to induce a dose-related inhibition of CRF-induced ACTH secretion, which is significant.

The administration of CRF antagonists reduces the spontaneous ACTH release observed after removal of the corticosteroid feedback, totally blocks the ACTH secretion caused by CRF, and inhibits most of the stress-induced ACTH release in intact rats. Such effects are comparable to those previously obtained with an antiserum to CRF which demonstrate the role played by endogenous CRF in regulating ACTH secretion, Rivier, C. et al., Science, 218, 377–9(1982).

Synthetic hCRF has been shown to be a powerful stimulator of secretion of ACTH and β-endorphin-like (β-END-LI) immunoactivities in vivo in several rat preparations. Plasma levels of ACTH and β-END-LI are elevated for at least 5–20 minutes following the intraveneous administration of hCRF to nembutal-anesthesized male rats and to quiescent male or female rats with indwelling intraveneous cannulae. In addition, hCRF is found to have a dramatic effect to lower blood pressure in rats and dogs when injected peripherally. These antagonists should counteract such effects.

EXAMPLE IV

The peptide [Aib$^{34}$]-rCRF having the formula (SEQ ID NO:4): Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Xaa-Arg-Lys-Leu-Met-Glu-Ile-Ile wherein the C-terminus is amidated and Xaa is Aib is synthesized using a procedure generally as set forth in Example I. The peptide stimulates the secretion of ACTH and β-END-LI and causes significant lowering of blood pressure when injected peripherally.

EXAMPLE V

Using the procedure as generally set forth in Example I, the following peptides are also prepared which are CRF antagonists:

[D-Ala$^{20}$]-AHC(9–41)
[Aib$^{34}$]-AHC(12–41)
[D-Ala$^{20}$]-oCRF(10–41)
[D-Phe$^{12}$, Aib$^{20}$, Nle$^{21,38}$]-rCRF(12–41)
[D-Phe$^{12}$, D-Ala$^{20}$]-oCRF(12–41)
[Nle$^{18,21}$, D-Ala$^{20}$]-AHC(10–41)
[D-Phe$^{12}$, D-Ala$^{20}$]-rCRF(12–41)
[D-Phe$^{12}$, Nle$^{21}$, Aib$^{34}$]-oRF(12–41)
[D-Phe$^{12}$, D-Ala$^{20}$]-AHC(12–41)
[D-Phe$^{12}$, Aib$^{22}$, Nle$^{21,38}$]-rCRF(12–41)
[D-Phe$^{12}$, Aib$^{24}$, Nle$^{21,38}$]-rCRF(12–41)
[D-Phe$^{12}$, Aib$^{28}$, Nle$^{21,38}$]-rCRF(12–41)
[D-Phe$^{12}$, Aib$^{29}$, Nle$^{21,38}$]-rCRF(12–41)
[D-Phe$^{12}$, Aib$^{31}$, Nle$^{21,38}$]-rCRF(12–41)
[D-Phe$^{12}$, Aib$^{32}$, Nle$^{21,38}$]-rCRF(12–41)
[D-Phe$^{12}$, Aib$^{34}$, Nle$^{21,38}$]-rCRF(12–41)
[D-Phe$^{12}$, Aib$^{39}$, Nle$^{21,38}$]-rCRF(12–41)
[D-Phe$^{12}$, Aib$^{40}$, Nle$^{21,38}$]-rCRF(12–41)
[Nle$^{18,21}$, D-Ala$^{20}$, D-His$^{32}$]-AHC(11–41)
[D-Phe$^{12}$, D-Glu$^{20}$, Aib$^{34}$]-rCRF(12–41)
[D-Ala$^{20}$, Nle$^{21,38}$]-rCRF(10–41)
[D-Phe$^{12}$, Nle$^{21,38}$, Aib$^{39}$]-oCRF(9–41)

| | |
|---|---|
| (c 17–20) | [Dbu$^{17}$, D-Glu$^{20}$, Nle$^{21,38}$, D-His$^{32}$]-rCRF(9–41) |
| " | [D-Phe$^{12}$, Asp$^{17}$, Nle$^{18,21}$, D-Dpr$^{20}$]-AHC(12-41) |
| " | [Glu$^{17}$, D-Lys$^{20}$, Nle$^{21}$, CML$^{37}$]-oCRF(11-41) |
| " | [Dpr$^{17}$, D-Asp$^{20}$, Nle$^{21,38}$ CML$^{37}$]-oCRF(10-41) |
| | [D-Phe$^{12}$, Aib$^{24}$, Nle$^{21,38}$, CML$^{37}$]-oCRF(12-41) |

These peptides are bipotent in inhibiting the secretion of ACTH and β-END-LI in response to various stimuli.

EXAMPLE VI

Using the procedure as generally set forth in Example I, the following peptides are also prepared which are CRF antagonists:

[CML$^{17}$]-AHC(12–41)
[CML$^{17}$]-oCRF(10–41)
[D-Phe$^{12}$, CML$^{14}$, Nle$^{21,38}$]-rCRF(12–41)
[D-Phe$^{12}$, CML$^{14}$]-oCRF(12–41)
[Nle$^{18,21}$, CML$^{17}$]-AHC(10–41)
[D-Phe$^{12}$, CML$^{17}$, D-Glu$^{20}$]-rCRF(12–41)
[D-Phe$^{12}$, Nle$^{21}$, CML$^{17,37}$]-oCRF(12–41)
[D-Phe$^{12}$, CML$^{15}$]-AHC(12–41)
[D-Phe$^{12}$, CML$^{15}$, Nle$^{21,38}$]-rCRF(12–41)
[D-Phe$^{12}$, CML$^{17}$, Nle$^{21,38}$]-rCRF(12–41)
[D-Phe$^{12}$, CML$^{17,37}$, Nle$^{21,38}$]-rCRF(12–41)
[Nle$^{18,21}$, CML$^{17,37}$, D-His$^{32}$]-AHC(11–41)
[D-Phe$^{12}$, CML$^{17,37}$, Aib$^{34}$]-rCRF(12–41)
[CML$^{17,37}$, Nle$^{21,38}$]-rCRF(10–41)
[D-Phe$^{12}$, CML$^{19}$]-rCRF(12–41)
[D-Phe$^{12}$, Nle$^{21}$, CML$^{27,37}$]-oCRF(12–41)

[D-Phe$^{12}$, CML$^{27}$]-AHC(12–41)
[D-Phe$^{12}$, CML$^{19}$, Nle$^{21,38}$]-rCRF(12–41)
[D-Phe$^{12}$, CML$^{27}$, Nle$^{21,38}$]-rCRF(12–41)
[D-Phe$^{12}$, CML$^{19,37}$, Nle$^{21,38}$]-rCRF(12–41)

These peptides are biopotent in inhibiting the secretion of ACTH and β-END-LI in response to various stimuli.

EXAMPLE VII

Using the procedure set forth in Example I, the following peptides are also prepared:
[Acetyl-Ser$^1$, D-Phe$^{12}$, D-Ala$^{20}$, Nle$^{21,38}$]-rCRF
[D-Phe$^{12}$, D-Ala$^{20}$]-oCRF
[D-Phe$^{12}$, D-Ala$^{20}$, D-Ala$^{24}$]-rCRF(4–41)
[D-Phe$^{12}$, Nle$^{21}$, Aib$^{34}$]-oCRF
[Formyl-Ser$^1$, D-Phe$^{12}$, D-Ala$^{20}$, Nle$^{21,38}$]-rCRF
[D-Ala$^{20}$, CML$^{17,37}$]-oCRF
[D-Phe$^{12}$, CML$^{17}$]-rCRF(2–41)
[D-Ala$^{20}$, Nle$^{21,38}$]-oCRF
[D-His$^{32}$, Aib$^{34}$]-oCRF
[D-Phe$^{12}$, D-Ala$^{20,24}$, D-His$^{32}$]-rCRF(6–41)
[Aib$^{20,29}$, Nle$^{21}$, D-His$^{32}$]-oCRF
[Acrylyl-Glu$^2$, D-Ala$^{20}$, Nle$^{21,38}$, D-His$^{32}$]-rCRF(2–41)
[Nle$^{18,21}$, D-Ala$^{20}$, D-His$^{32}$]-AHC
[D-Pro$^4$, D-Phe$^{12}$, Nle$^{18,21}$, D-Ala$^{20}$]-AHC(4–41)
[D-Tyr$^3$, Nle$^{18}$, Nva$^{21}$, D-Ala$^{20}$]-AHC

| (c 17-20) | [Glu$^{17}$, Nle$^{18,21}$, D-Orn$^{20}$]-AHC |
| --- | --- |
| " | [D-Phe$^{12}$, Glu$^{17}$, D-Dpr$^{20}$]-AHC |
| " | [D-Phe$^{12}$, Lys$^{17}$, D-Asp$^{20}$]-AHC |
| " | [Nle$^{18,21}$, Asp$^{17}$, D-Dpr$^{20}$]-AHC |
| " | [Dbu$^{17}$, D-Asp$^{20}$]-AHC |
| " | [Orn$^{17}$, D-Glu$^{20}$]-AHC |
| " | [Dpr$^{17}$, D-Glu$^{20}$, Nle$^{21}$, CML$^{37}$]-oCRF |
| " | [D-Phe$^{12}$, Asp$^{17}$, D-Orn$^{20}$, Nle$^{21,38}$, CML$^{37}$]-oCRF |
| " | [Dpr$^{17}$, D-Glu$^{20}$, Nle$^{21,38}$, CML$^{37}$]-oCRF |

These peptides are biopotent in stimulating the secretion of ACTH and β-END-LI.

CRF profoundly stimulates the pituitary-adrenalcortical axis, and CRF agonists should be useful to stimulate the functions of this axis in some types of patients with low endogenous glucocorticoid production. For example, CRF agonists should be useful in restoring pituitary-adrenal function in patients having received exogenous glucocorticoid therapy whose pituitary-adrenalcortical functions remain supressed. CRF antagonists should be useful to inhibit the functions of this axis in some types of patients with high ACTH and endogeous glucocorticoid production. For example, CRF antagonists may be useful in regulating pituitary-adrenal function in patients having pituitary Cushings disease or any CRF-sensitive tumor.

Most other regulatory peptides have been found to have effects upon the endocrine system, the central nervous system and upon the gastrointestinal tract. Because ACTH and β-END-LI secretion is the "sine qua non" of mammal's response to stress, it was not surprising that CRF has significant effects on the brain as a mediator of many of the body's stress responses. Accordingly, CRF antagonists delivered to the brain should also find application in modifying the mood, learning and behavior of normal and mentally disordered individuals. Furthermore, CRF antagonists in the brain could ameliorate stress-induced conditions to which endogenous CRF might contribute, including some types of hypertension, infertility, decreased libido, impotency and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function.

All CRF-related peptides have been shown to dialate the mesenteric vascular bed. CRF antagonists may also be of use for decreasing blood flow to the gastrointestinal tract of mammals, particularly humans. Also, oCRF influences gastric acid production, and CRF antagonists are expected to also be effective to modulate gastrointestinal functions.

CRF antagonists or the nontoxic addition salts thereof, combined with a pharmaceutically or veterinarily acceptable carrier to form a pharmaceutical composition, may be administered to mammals, including humans, either intravenously, subcutaneously, intramuscularly, percutaneously, e.g. intranasally, intracerebroventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous gluco-corticoid production or for possible uses outlined above. The required dosage will vary with the particular condition being treated, with the severity of the condition and with the duration of desired treatment. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 0.01 to about 10 milligrams of the peptide per kilogram of the body weight of the host animal. As used herein all temperatures are ° C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the antagonists. For instance, instead of the simple amide at the C-terminal, a lower alkyl-substituted amide, e.g. 1–4 carbon atoms, i.e. methylamide, ethylamide, etc. may be incorporated. Such peptides are considered as being within the scope of the invention.

Various features of the invention are emphasized in the claims which follow.

---

What is claimed is:

1. A CRF peptide antagonist having the formula:

D—Phe—His—Leu—Leu—Arg—R$_{17}$—Val—Leu—R$_{20}$—
—Nle—Ala—Arg—Ala—Glu—Gln—Leu—Ala—Gln—
—Gln—Ala—His—Ser—Asn—Arg—Lys—Leu—Nle—
—Glu—Ile—Ile—NH$_2$ wherein R$_{17}$ is Cys, Glu, Asp, Dpr, Dbu or Lys; R$_{20}$ is D-Cys, D-Glu, D-Asp, D-Dpr, D-Dbu or D-Lys; or a nontoxic addition salt thereof.

2. A CRF peptide antagonist having the formula:

H—D—Phe—His—Leu—Leu—Arg—Cys—Val—Leu—D—Cys—Nle—Ala—Arg—
Ala—Glu—Gln—Leu—Ala—Gln—Gln—Ala—His—Ser—Asn—Arg—Lys—Leu—
Nle—Glu—Ile—Ile—NH$_2$.

3. A CRF peptide antagonist having the formula: H-D-Phe-His-Leu-Leu-Arg-Glu-Val-Leu-D-Ala-Nle-Ala-Arg-Ala-Glu-Gln-Leu-Ala-Gln-Gln-Ala-His-Ser-Asn-Arg-Lys-Leu-Nle-Glu-Ile-Ile-NH$_2$.

* * * * *

UNITED STATES PATENT AND TRADEMARK OFFICE
CERTIFICATE OF CORRECTION

PATENT NO. : 5,245,009
DATED : September 14, 1993
INVENTOR(S) : Kornreich, et al It is certified that error appears in the above-indentified patent and that said Letters Patent is hereby corrected as shown below:

On the Title Page, Item [57];
Line 14, change "Try;" to --Tyr;--.

Column 1, line 36, change "c-terminus" to -- C-terminus --; line 44, change "-Lsy-" to -- -Lys- --. Column 2, line 61, change "$R_{18}$" to --$R_{17}$--. Column 3, line 32 change "D-Phe12, CML15," to -- D-Phe$^{12}$, CML$^{15}$, --. Column 4, line 25, change "Glyn;" to --Gln;--. Column 5, line 57, change "or" to --of--. Column 6, line 6, change "Fmox;" to --Fmoc;--; line 17, change "alph-amino" to --alpha-amino--. Column 8, line 42, change "preferably" to --preferable--; line 66, change "4,144.805" to --4,133,805--. Column 10, line 24, change "ilnkage" to --linkage--; line 46, change "Plarimeter" to --Polarimeter--. Column 12, line 22, change "-oRF" to --oCRF--. Column 13, line 49, change "endogeous" to --endogenous--.

Signed and Sealed this

Tenth Day of May, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,245,009
DATED : September 14, 1993
INVENTOR(S) : Kornreich, et. al.

It is certified that error appears in the above-indentified patent and that said Letters Patent is hereby corrected as shown below:

On the Title page: The date in the Notice, the date should be -- April 28, 2009--.

Signed and Sealed this

Eleventh Day of October, 1994

Attest:

BRUCE LEHMAN

*Attesting Officer*   *Commissioner of Patents and Trademarks*